United States Patent
O'Halloran et al.

(10) Patent No.: US 9,895,233 B2
(45) Date of Patent: *Feb. 20, 2018

(54) INTERVERTEBRAL NUCLEUS AND ANNULUS IMPLANTS AND METHODS OF USE THEREOF

(71) Applicant: GLOBUS MEDICAL, INC., Audubon, PA (US)

(72) Inventors: Damien O'Halloran, Conshohocken, PA (US); Jody L. Seifert, Birdsboro, PA (US); Jeff Bennett, Pottstown, PA (US); Aditya Ingalhalikar, Norristown, PA (US); Sean Suh, Morganville, NJ (US); Sophia Tetteh, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/425,236

(22) Filed: Feb. 6, 2017

(65) Prior Publication Data
US 2017/0143505 A1    May 25, 2017

Related U.S. Application Data

(63) Continuation of application No. 14/618,003, filed on Feb. 10, 2015, now Pat. No. 9,597,193, which is a
(Continued)

(51) Int. Cl.
  A61F 2/44    (2006.01)
  A61F 2/46    (2006.01)
  A61F 2/30    (2006.01)

(52) U.S. Cl.
  CPC .......... *A61F 2/442* (2013.01); *A61F 2/30767* (2013.01); *A61F 2/441* (2013.01); *A61F 2/4611* (2013.01); *A61F 2002/302* (2013.01); *A61F 2002/30064* (2013.01); *A61F 2002/30069* (2013.01); *A61F 2002/3082* (2013.01); *A61F 2002/30224* (2013.01); *A61F 2002/30291* (2013.01); *A61F 2002/30565* (2013.01); *A61F 2002/30586* (2013.01); *A61F 2002/30588* (2013.01); *A61F 2002/30616* (2013.01); *A61F 2002/30677* (2013.01); *A61F 2002/30841* (2013.01); *A61F 2002/444* (2013.01);
(Continued)

(58) Field of Classification Search
  CPC ..... A61F 2/442; A61F 2/441; A61F 2002/444
  See application file for complete search history.

(56) References Cited

U.S. PATENT DOCUMENTS 5,192,326 A * 3/1993 Bao .......................... A61F 2/441
                                                         623/17.12
5,549,679 A * 8/1996 Kuslich .............. A61B 17/7098
                                                         606/247
(Continued)

*Primary Examiner* — Christian Sevilla

(57) ABSTRACT

The invention encompasses devices and methods for treating one or more damaged, diseased, or traumatized intervertebral discs to reduce or eliminate associated back pain. Specifically, the invention encompasses intervertebral nucleus and annulus implants that are resistant to migration in and/or expulsion from an intervertebral disc space. The invention further encompasses kits including the implantable devices of the invention and associated delivery tools to treat annular and nuclear tissue.

20 Claims, 12 Drawing Sheets

Related U.S. Application Data continuation of application No. 12/725,988, filed on Mar. 17, 2010, now Pat. No. 9,039,769.

(52) U.S. Cl.
CPC ............... *A61F 2002/4435* (2013.01); *A61F 2002/4622* (2013.01); *A61F 2002/4635* (2013.01); *A61F 2230/0065* (2013.01); *A61F 2230/0091* (2013.01); *A61F 2310/00017* (2013.01); *A61F 2310/00023* (2013.01); *A61F 2310/00029* (2013.01); *A61F 2310/00059* (2013.01); *A61F 2310/00071* (2013.01)

(56) References Cited

U.S. PATENT DOCUMENTS

| | | | | |
|---|---|---|---|---|
| 5,755,797 A | * | 5/1998 | Baumgartner | ......... A61F 2/441 623/17.16 |
| 2006/0052874 A1 | * | 3/2006 | Johnson | ................ A61F 2/441 623/17.16 |
| 2006/0293749 A1 | * | 12/2006 | Hudgins | ................ A61F 2/441 623/17.11 |

* cited by examiner

INTERVERTEBRAL NUCLEUS AND ANNULUS IMPLANTS AND METHODS OF USE THEREOF

CROSS-REFERENCE TO RELATED APPLICATIONS

The present application is a continuation of U.S. patent application Ser. No. 14/618,003 filed on Feb. 10, 2015 which is a continuation of U.S. patent application Ser. No. 12/725,988, filed Mar. 17, 2010, and entitled "Intervertebral Nucleus and Annulus Implants and Method of Use Thereof." The entire applications are hereby incorporated by reference in its entirety.

FIELD OF THE INVENTION

The invention encompasses devices and methods for treating one or more damaged, diseased, or traumatized intervertebral discs to reduce or eliminate associated back pain. Specifically, the invention encompasses intervertebral nucleus pulposus and annulus fibrosus implants that are resistant to migration in and/or expulsion from an intervertebral disc space. The invention further encompasses kits including the implantable devices of the invention and associated delivery tools to treat annular and nuclear tissue.

BACKGROUND OF THE INVENTION

The spinal column is formed from a number of bony vertebrae, which in their normal state are separated from each other by intervertebral discs. Intervertebral discs provide mobility and a cushion between the vertebrae. These discs are comprised of the annulus fibrosus and the nucleus pulposus both of which are soft tissue. At the center of the disc is the nucleus pulposus. The nucleus pulposus is surrounded by the annulus fibrosus, which is comprised of cells (fibrocyte-like and chondrocyte-like), collagen fibers, and non-fibrillar extracellular matrix. The intervertebral disc acts in the spine as a stabilizer and as a mechanism for force distribution between adjacent vertebral bodies. Without a competent disc, collapse of the intervertebral disc may occur contributing to abnormal joint mechanics and premature development of degenerative and/or arthritic changes.

The normal intervertebral disc has an outer ligamentous ring called the annulus surrounding the nucleus pulposus. The annulus binds the adjacent vertebrae together and is constituted of collagen fibers that are attached to the vertebrae and cross each other so that half of the individual fibers will tighten as the vertebrae are rotated in either direction, thus resisting twisting or torsional motion. The nucleus pulposus is constituted of soft tissue, having about 85% water content, which moves about during bending from front to back and from side to side.

The aging process contributes to gradual changes in the intervertebral discs. The annulus loses much of its flexibility and resilience, becoming more dense and solid in composition. The aging annulus may also be marked by the appearance or propagation of cracks or fissures in the annular wall. Similarly, the nucleus desiccates increasing viscosity and thus losing its fluidity. In combination, these features of the aged intervertebral discs result in less dynamic stress distribution because of the more viscous nucleus pulposus, and less ability to withstand localized stresses by the annulus fibrosus due to its desiccation, loss of flexibility and the presence of fissures. Fissures can also occur due to disease or other pathological conditions. Occasionally fissures may form rents through the annular wall. In these instances, the nucleus pulposus is urged outwardly from the subannular space through a rent, often into the spinal column. Extruded nucleus pulposus can and often does mechanically press on the spinal cord or spinal nerve rootlet. This painful condition is clinically referred to as a ruptured or herniated disc.

In the event of annulus rupture, the subannular nucleus pulposus migrates along the path of least resistance forcing the fissure to open further, allowing migration of the nucleus pulposus through the wall of the disc, with resultant nerve compression and leakage of chemicals of inflammation into the space around the adjacent nerve roots supplying the extremities, bladder, bowel and genitalia. The usual effect of nerve compression and inflammation is intolerable back or neck pain, radiating into the extremities, with accompanying numbness, weakness, and in late stages, paralysis and muscle atrophy, and/or bladder and bowel incontinence. Additionally, injury, disease or other degenerative disorders may cause one or more of the intervertebral discs to shrink, collapse, deteriorate, or become displaced, herniated, or otherwise damaged and compromised. There are a number of suspected causes of disc related pain, and in any given patient, one or more of these causes may be present.

The inventors have developed compositions for the treatment of disc related disorders, particularly in the treatment of disc related pain associated with a damaged or otherwise unhealthy disc.

SUMMARY OF THE INVENTION

The inventors have surprisingly found that the compositions and methods of the invention for annulus fibrosus and nucleus pulposus replacement and repair overcome the shortcomings associated with currently used replacement and repair technology.

Accordingly, in one embodiment, the invention encompasses a nucleus pulposus replacement composition comprising an elastomeric or polymeric material comprising a central cavity; a plurality of elastomeric beads; and a biocompatible fluid or gel. In certain exemplary embodiments, the nucleus pulposus replacement composition is in the form of a balloon, and the plurality of elastomeric beads is suspended in the biocompatible fluid or gel and fills a central cavity of the nucleus pulposus replacement composition. In other exemplary embodiments, the balloon is fillable in situ to conform to the dimensions of an intevertebral disc space and to an inner wall of an annulus fibrosus.

In another embodiment, the invention encompasses a nucleus pulposus replacement composition comprising one or more biocompatible polymeric or elastomeric materials in the form of a pre-shaped balloon. In certain embodiments, the nucleus pulposus replacement composition includes a central cavity and one or more envelope cavities surrounding the central cavity. In certain embodiments, the biocompatible polymeric or elastomeric material comprises a solid, deformable, and load-bearing material.

In another embodiment, the invention encompasses a nucleus pulposus replacement composition comprising one or more biocompatible polymeric or elastomeric materials in the form of a plurality of concentric coils that are conically shaped, wherein the outermost perimeter of the plurality of concentric coils is capable of conforming to an inner wall of an annulus fibrosus. In certain embodiments, the nucleus replacement composition is comprised of a biocompatible polymeric or elastomeric material coiled into a plurality of concentric coils of narrowing diameter (e.g., conically shaped), which are deformable and load-bearing.

In another embodiment, the invention encompasses a nucleus pulposus replacement composition comprised of one or more biocompatible polymeric or elastomeric materials in the shape of a plurality of string-like implants. In certain embodiments, the nucleus pulposus replacement composition is comprised of a plurality of string-like implants comprised of elastomeric microbeads that form a cylindrical string, which are deformable and load-bearing.

In another embodiment, the invention encompasses a nucleus pulposus containment shell comprising:

a. an outer shell comprised of a biocompatible material;

b. an inner surface capable of being filled with a load bearing polymeric or elastomeric material, c. a unidirectional valve to allow filling of the inner surface; and d. a sealing crimp to prevent leakage of the load bearing polymeric or elastomeric material filling the inner surface.

wherein the outer shell has an cylindrical-like or ellipsoid-like shape and wherein a top surface and/or a bottom surface of the outer shell are textured to provide anchorage with one or more vertebral endplates.

In another embodiment, the invention encompasses a nucleus pulposus containment shell comprising:

a. an outer shell comprised of a biocompatible material;

b. an inner surface capable of being filled with a load bearing polymeric or elastomeric material, c. a unidirectional valve to allow filling of the inner surface; and d. a sealing crimp to prevent leakage of the load bearing polymeric or elastomeric material filling the inner surface.

wherein the outer shell has an tubular ring-like shape (i.e., donut-shaped including a central orifice), wherein a top surface and/or a bottom surface of the outer shell are textured to provide anchorage with one or more vertebral endplates.

In another embodiment, the invention encompasses a combination nucleus pulposus replacement and annulus fibrosus repair system comprising:

a. nucleus replacement composition comprising:

i. an outer surface comprised of a biocompatible material and adapted to conform to an inner wall of an annulus fibrosus and comprising a valve attached to the outer surface comprising a rigid socket geometry; and ii. an inner surface having a central recess capable of receiving a load bearing polymeric or elastomeric material, wherein the outer and inner surfaces define a solid, deformable thickness therebetween; and b. an annulus fibrosus plug comprising a ball-fitting that connects with the valve of the nucleus replacement composition, wherein the ball fitting comprises a plug of a natural or synthetic material that promotes cell in-growth with the surrounding annulus fibrosus.

In another embodiment, the invention encompasses a method of replacing a nucleus pulposus and repairing an annulus fibrosus comprising:

a. removing the nucleus pulposus through an opening in the annulus fibrosus to create a nucleus cavity;

b. inserting a nucleus pulposus replacement composition comprising a fillable central cavity into the nucleus cavity;

c. filling a plurality of elastomeric beads suspended in a biocompatible fluid or gel into the nucleus pulposus replacement composition; and d. plugging the annulus fibrosus.

BRIEF DESCRIPTION OF THE FIGURES

A more complete understanding of the present invention may be obtained by reference to the accompanying drawings, when considered in conjunction with the subsequent detailed description. The embodiments illustrated in the drawings are intended only to exemplify the invention and should not be construed as limiting the invention to the illustrated embodiments, in which.

DETAILED DESCRIPTION OF THE INVENTION

Figure 1A:
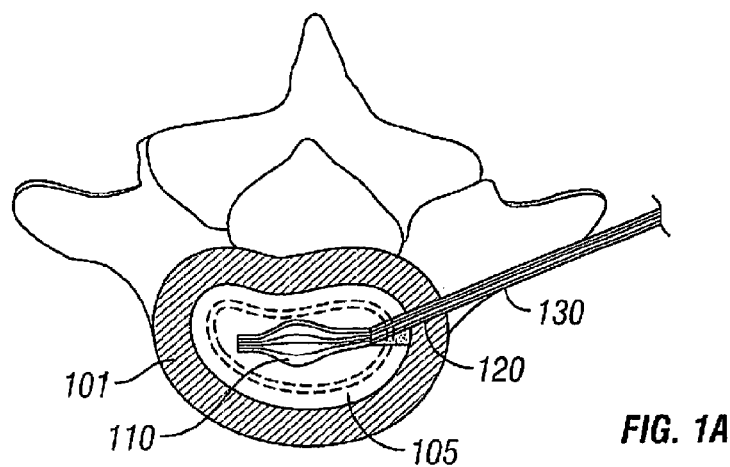
FIG. 1a illustrates a non-limiting, exemplary schematic of the insertion of a deflated single- or multi-lumen biocompatible polymeric or elastomeric balloon into the nucleus pulposus cavity using a catheter or endoscope.

The invention generally encompasses nucleus pulposus and annulus fibrosus replacement and repair technology.

In one embodiment, the invention encompasses a nucleus pulposus replacement composition comprising one or more elastomeric or polymeric materials comprising a central fillable cavity; a plurality of elastomeric beads; and a biocompatible fluid or gel, wherein the plurality of elastomeric beads are suspended in the biocompatible fluid or gel and each fill the central cavity of the nucleus pulposus replacement composition.

In certain illustrative embodiments, the nucleus pulposus replacement composition is in the form of a balloon.

In certain illustrative embodiments, the central fillable cavity is filled in situ to conform to the dimensions of an intevertebral disc space and to an inner wall of an annulus fibrosus.

In certain illustrative embodiments, the central fillable cavity is pre-shaped with dimensions that conform to an intevertebral disc space corresponding to an inner wall of an annulus fibrosus such that upon filling the central cavity the nucleus pulposus replacement composition will conform to the walls of the annulus fibrosus.

In certain illustrative embodiments, the central fillable cavity comprises a single lumen.

In certain illustrative embodiments, the central fillable cavity comprises more than one lumen.

In certain illustrative embodiments, the central fillable cavity comprises a central cavity and one or more envelope cavities surrounding the central cavity.

In certain illustrative embodiments, the one or more biocompatible polymers or elastomers comprise thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, styrene isoprene butadiene, and combinations thereof.

In certain illustrative embodiments, the central cavity and one or more envelope cavities surrounding the center cavity can be independently filled with a plurality of elastomeric beads and the biocompatible fluid or gel. In certain embodiments, the plurality of elastomeric beads is suspended in the biocompatible fluid.

In certain illustrative embodiments, the elastomeric beads are comprised of silicone, urethane, silicone-urethane copolymer, polycarbonate-urethane copolymer, polyethylene terephthalate, or combinations thereof.

In certain illustrative embodiments, the biocompatible fluid or gel is saline, beta-glucan, hyaluronic acid and derivatives thereof, polyvinyl pyrrolidone or a hydrogel derivative thereof, dextrans or a hydrogel derivative thereof, glycerol, polyethylene glycol, Pluronic® type block copolymers (i.e., based on ethylene oxide and propylene oxide), polyvinyl acetate, succinaylated collagen, liquid collagen, and other polysaccharides or biocompatible polymers or combinations thereof.

In certain illustrative embodiments, the composition is porous.

In certain illustrative embodiments, the porous composition further comprises one or more bioactive agents, which diffuse into the surrounding tissue after implantation.

In certain illustrative embodiments, the one or more bioactive agents promote growth or reduce inflammation.

In another embodiment, the invention encompasses a nucleus pulposus replacement composition comprising one or more biocompatible polymeric or elastomeric materials in the form of a pre-shaped balloon, wherein the biocompatible elastomeric or polymeric material comprises a central cavity and one or more envelope cavities surrounding the center cavity.

In certain illustrative embodiments, one or more biocompatible polymeric or elastomeric material comprises thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the center cavity and one or more envelope cavities surrounding the center cavity can be independently filled with a plurality of elastomeric beads and/or a biocompatible fluid or gel.

In certain illustrative embodiments, the elastomeric beads are comprised of silicone, urethane, silicone-urethane copolymer, polycarbonate-urethane copolymer, polyethylene terephthalate, or combinations thereof.

In certain illustrative embodiments, the biocompatible fluid or gel is comprised of saline, beta-glucan, hyaluronic acid and derivatives thereof, polyvinyl pyrrolidone or a hydrogel derivative thereof, dextrans or a hydrogel derivative thereof, glycerol, polyethylene glycol, Pluronic® type block copolymers (i.e., based on ethylene oxide and propylene oxide), succinaylated collagen, liquid collagen, and other polysaccharides or biocompatible polymers or combinations thereof.

In certain illustrative embodiments, the composition is porous. In certain illustrative embodiments, the porous composition further comprises one or more bioactive agents, which diffuse into the surrounding tissue after implantation.

In certain illustrative embodiments, one or more bioactive agents promote growth or reduce inflammation.

In another embodiment, the invention encompasses a nucleus pulposus replacement composition comprising one or more biocompatible polymeric or elastomeric materials conically shaped in the form of a plurality of concentric coils of narrowing diameter, wherein the outermost perimeter conforms to an inner wall of an annulus fibrosus.

In certain illustrative embodiments, the one or more biocompatible polymeric or elastomeric material comprises thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the composition has a height that conforms with a vertebral disc height.

In certain illustrative embodiments, the composition is porous.

In certain illustrative embodiments, the porous composition further comprises one or more bioactive agents, which diffuse into the surrounding tissue after implantation.

In certain illustrative embodiments, the one or more bioactive agents promote growth or reduce inflammation.

In another embodiment, the invention encompasses a nucleus replacement composition comprised of one or more biocompatible elastomeric or polymeric materials in the shape of a plurality of string-like implants.

In certain illustrative embodiments, the string-like implants are formed from a plurality of microbeads that form a cylindrical string.

In certain illustrative embodiments, the one or more biocompatible elastomeric or polymeric materials comprise thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the microbeads are comprised of silicone, urethane, silicone-urethane copolymer, polycarbonate-urethane copolymer, polyethylene terephthalate, or combinations thereof.

In certain illustrative embodiments, the composition is porous.

In certain illustrative embodiments, the porous composition further comprises one or more bioactive agents, which diffuse into the surrounding tissue after implantation.

In certain illustrative embodiments, the one or more bioactive agents promote growth or reduce inflammation.

In another embodiment, the invention encompasses a nucleus pulposus containment shell comprising:
a. an outer shell comprised of a biocompatible material;
b. an inner surface capable of receiving a load bearing polymeric or elastomeric material,
c. a unidirectional valve to allow filling of the inner surface; and
d. a sealing crimp to prevent leakage of the load bearing polymeric or elastomeric material filling the inner surface.
wherein the outer shell has an cylindrical-like shape,
wherein a top surface and/or a bottom surface of the outer shell are textured to provide anchorage with one or more vertebral endplates.

In certain illustrative embodiments, the outer shell is comprised of a metallic foil-like material comprised NiTi alloy, stainless steel, titanium or combinations thereof.

In certain illustrative embodiments, the outer shell is comprised of a polymeric material, a biodegradable or bioresorbable material, or a combination thereof.

In certain illustrative embodiments, the polymeric material is polypropylene, polyethylene, polyurethane, polycarbonate urethane, Polyetheretherketone (PEEK), polyester, PET, poly olefin copolymer, polypropylene, polyethylene or a combination thereof.

In certain illustrative embodiments, the biodegradable or bioresorbable material is collagen, cellulose, polysaccharide, polyglycolic acid (PGA), a polylevolactic acid (PPLA), a polydioxanone (PDA), polylactic acid (PDLLA) or a combination thereof.

In certain illustrative embodiments, the load bearing polymeric or elastomeric material is thermoplastic polyurethane elastomer, poly siloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, silicone, urethane, silicone-urethane copolymer, polycarbonate-urethane copolymer, polyethylene terephthalate, saline, beta-glucan, hyaluronic acid and derivatives thereof, polyvinyl pyrrolidone or a hydrogel derivative thereof, dextrans or a hydrogel derivative thereof, glycerol, polyethylene glycol, succinaylated collagen, liquid collagen, and other polysaccharides or biocompatible polymers or combinations thereof.

In certain illustrative embodiments, the composition is porous.

In certain illustrative embodiments, the porous composition further comprises one or more bioactive agents, which slowly diffuse into the surrounding tissue after implantation.

In certain illustrative embodiments, the one or more bioactive agents promote growth or reduce inflammation.

In another embodiment, the invention encompasses a nucleus pulposus containment shell comprising:
 a. an outer shell comprised of a biocompatible material;
 b. an inner surface capable of receiving a load bearing polymeric or elastomeric material,
 c. a unidirectional valve for filling the inner surface; and
 d. a sealing crimp to prevent leakage of the load bearing polymeric or elastomeric material filling the inner surface.
  wherein the outer shell has an tubular ring-like shape, wherein a top surface and/or a bottom surface of the outer shell are textured to provide anchorage with vertebral endplates.

In certain illustrative embodiments, the outer shell is comprised of a metallic foil-like material comprised NiTi alloy, stainless steel, titanium or combinations thereof.

In certain illustrative embodiments, the outer shell is comprised of a polymeric material, a biodegradable or bioresorbable material, or a combination thereof.

In certain illustrative embodiments, the polymeric material is polypropylene, polyethylene, polyurethane, polycarbonate urethane, Polyetheretherketone (PEEK), polyester, PET, poly olefin copolymer, polypropylene, polyethylene or a combination thereof.

In certain illustrative embodiments, the biodegradable or bioresorbable material is collagen, cellulose, polysaccharide, polylactic acid (PLA), polyglycolic acid (PGA), polylactic acid/polyglycolic acid, a polylevolactic acid (PPLA), a polydioxanone (PDA), polylactic acid (PDLLA) or a combination thereof.

In certain illustrative embodiments, the load bearing polymeric or elastomeric material is thermoplastic polyurethane elastomer, poly siloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, silicone, urethane, silicone-urethane copolymer, polycarbonate-urethane copolymer, polyethylene terephthalate, saline, beta-glucan, hyaluronic acid and derivatives thereof, polyvinyl pyrrolidone or a hydrogel derivative thereof, dextrans or a hydrogel derivative thereof, glycerol, polyethylene glycol, Pluronic® type block copolymers (i.e., based on ethylene oxide and propylene oxide), succinaylated collagen, liquid collagen, and other polysaccharides or biocompatible polymers or combinations thereof.

In certain illustrative embodiments, the composition is porous.

In certain illustrative embodiments, the porous composition further comprises one or more bioactive agents, which slowly diffuse into the surrounding tissue after implantation.

In certain illustrative embodiments, the one or more bioactive agents promote growth or reduce inflammation.

In another embodiment, the invention encompasses a combination nucleus pulposus replacement and annulus fibrosus repair system comprising:
 a. nucleus replacement composition comprising:
  i. an outer surface comprised of a biocompatible material and adapted to conform to an inner wall of an annulus fibrosus and comprising a valve attached to the outer surface comprising a rigid socket geometry; and
  ii. an inner surface having a central recess capable of receiving a load bearing polymeric or elastomeric material, wherein the outer and inner surfaces define a solid, deformable thickness therebetween; and
 b. an annulus fibrosus plug comprising a ball fitting that connects with the valve of the nucleus replacement composition, wherein the ball fitting comprises a plug of a natural or synthetic material that promotes cell in-growth with the surrounding annulus fibrosus.

In certain illustrative embodiments, the ball fitting of the annulus fibrosus plug can be formed of other shaped fittings, for example, an elliptical fitting.

In certain illustrative embodiments, the repair system further comprises a guide for inserting and/or connecting the annulus fibrosus plug with the nucleus replacement composition.

In certain illustrative embodiments, the rigid socket geometry is comprised of a metal, plastic (e.g., polyether ether ketone) or combination thereof.

In another embodiment, the invention encompasses a method of replacing a nucleus pulposus comprising:
 a. removing the nucleus pulposus through an opening in the annulus fibrosus to create a nucleus cavity;
 b. inserting a nucleus pulposus replacement composition comprising a fillable central cavity into the nucleus cavity;
 c. filling elastomeric beads suspended in a biocompatible fluid or gel into the nucleus pulposus replacement composition; and
 d. plugging the annulus fibrosus.

In certain illustrative embodiments, the removing of the nucleus pulposus is done using forceps.

In certain illustrative embodiments, the inserting a nucleus pulposus replacement composition is done using an endoscope or catheter.

In certain illustrative embodiments, the opening in the annulus is through a tear or injury in the annulus fibrosus.

In certain illustrative embodiments, the nucleus pulposus replacement composition is comprised of one or more biocompatible elastomers comprised of thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the nucleus pulposus replacement composition is in the form of an inflatable balloon.

In certain illustrative embodiments, the inflatable balloon comprises one or more lumen.

In certain illustrative embodiments, the elastomeric beads are comprised of silicone, urethane, silicone-urethane copolymer, polycarbonate-urethane copolymer, polyethylene terephthalate, or combinations thereof.

In certain illustrative embodiments, the biocompatible fluid or gel is beta-glucan, hyaluronic acid and derivatives thereof, polyvinyl pyrrolidone or a hydrogel derivative thereof, dextrans or a hydrogel derivative thereof, glycerol, polyethylene glycol, Pluronic® type block copolymers (i. e., based on ethylene oxide and propylene oxide), succinaylated collagen, liquid collagen, and other polysaccharides or biocompatible polymers or combinations thereof.

In certain embodiments, the plugging of annulus fibrosus comprises sutures (e.g., resorbable or non-resorbable strips/cords/draw strings/wires/cords), scaffolds (e.g., fibrous weaved textiles), adhesives (e.g., fibrin, cyanoacrylates, polyanhydrides, glutaraldehydes, PRP), in-situ fabricated plugs (e.g., single sheet wound or two piece snapped together), pre-fabricated plugs, expandable plugs (e.g., stent like), or combinations thereof.

Nucleus Replacement Technology of the Invention

The invention generally encompasses nucleus pulposus replacement compositions that can be implanted with minimally invasive surgical procedures. Due to the composition, make-up and mechanical properties (e.g., flexibility and compressibility), the nucleus pulposus replacement compositions of the invention will result in less blood loss during implantation, shorter post-operative recovery times, and shorter surgical operation time.

In one embodiment, the invention encompasses a nucleus pulposus replacement composition including a solid, deformable, load-bearing material (e.g., an elastomeric balloon) and a plurality of elastomeric beads suspended in a biocompatible fluid or gel.

The nucleus pulposus replacement composition is useful for treating or replacing one or more herniated or degenerated discs. In an illustrative embodiment, the nucleus pulposus replacement composition is used in minimally invasive endoscopic disectomy (e.g., lumbar disectomy) for treating or replacing one or more herniated or degenerated discs. The nucleus pulposus replacement composition can support the annulus fibrosus and maintain its structural and functional integrity. To repair an injury, the nucleus material leaking from the opening or tear in the annulus fibrosus is removed in a minimally invasive surgical operation to form a nucleus cavity. This may be carried out with, for example, a forceps-like instrument with which the jelly-like nucleus material is cut off and the opening may also be enlarged and its edges smoothed. The nucleus pulposus replacement composition of the invention can then be inserted into the cavity as described herein.

In certain illustrative embodiments, the nucleus pulposus replacement composition incorporates a deflated deformable, load-bearing material (e.g., a single or multi-lumen elastomeric balloon), which can be inflated with an elastomeric material (e.g., elastomeric beads or balls) suspended in a biocompatible fluid or gel. The elastomeric material suspended in a biocompatible fluid or gel can be dispensed into the nucleus pulposus replacement composition using an endoscope or catheter.

In certain illustrative embodiments, the nucleus pulposus replacement composition can mimic the nucleus pulposus of a healthy subject and will bear physiologic loads through stiffness imparted by the elastomeric beads or balls and the hydrostatic pressure generated by the biocompatible fluid or gel. The stiffness and internal hydrostatic pressure can assist load bearing, support the annulus fibrosus from all sides and prevent creep or effusion and stress relaxation of the elastomeric material. Motion can be achieved through the existing annulus and the deformation of the nucleus.

Figure 1B:
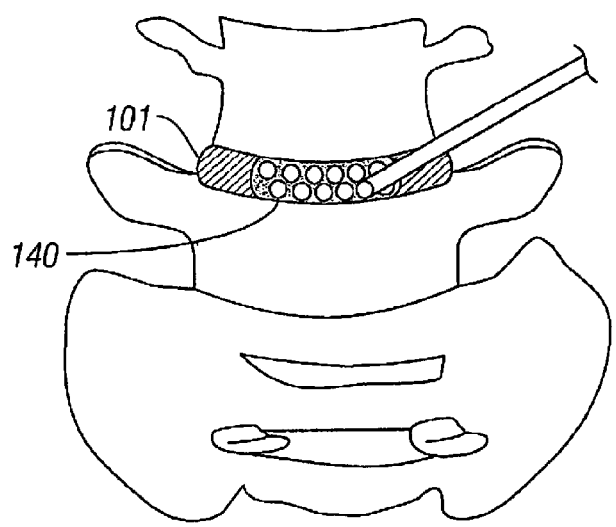
FIG. 1b illustrates the inflating of the balloon using mechanical or hydraulic means with load bearing microbeads suspended in biocompatible fluid or gel.
Figure 1C:
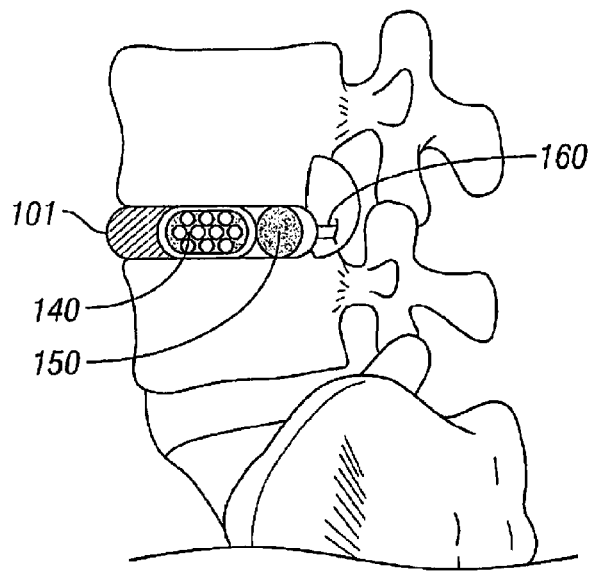
FIG. 1c illustrates the plugging of the annular injury using a catheter or endoscope.

FIG. 1 illustrates a non-limiting, exemplary schematic of the insertion. In FIG. 1a, a deflated single- or multi-lumen balloon 110 can be inserted into the nucleus pulposus cavity 105 using a catheter or endoscope 130. FIG. 1b illustrates the inflating of the balloon using mechanical or hydraulic means with load bearing microbeads 140 suspended in biocompatible fluid or gel. FIG. 1c illustrates the plugging of the annular injury and removal of the catheter or endoscope.

FIGS. 1b and 1c also illustrate the inflated nucleus pulposus replacement composition arranged between two vertebrae. The intervertebral disc consists of the central nucleus and the annulus fibrosus surrounding it. It is understood that the upper vertebra rests with its lower end plate in a surface-to-surface manner in the same way as the lower vertebra with its upper end plate against the intervertebral disc. FIG. 1c shows schematically how through an opening 150 in the annulus fibrosus, for example, in the form of a tear, the nucleus pulposus replacement composition can be inserted.

The nucleus pulposus replacement composition comprising a solid, deformable, load-bearing material can be comprised of any durable material that is safe for in vivo transplantation including, but not limited to, one or more biocompatible polymers of elastomers including thermoplastic polyurethane elastomer, poly siloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the plurality of elastomeric beads or balls include any material that is safe for in vivo use including, but not limited to, silicone, urethane, silicone-urethane copolymer, polycarbonate-urethane copolymer, polyethylene terephthalate, or combinations thereof.

In other illustrative embodiments, the biocompatible fluid or gel include any material that is safe for in vivo use including, but not limited to, saline, beta-glucan, hyaluronic acid and derivatives thereof, polyvinyl pyrrolidone or a hydrogel derivative thereof, dextrans or a hydrogel derivative thereof, glycerol, polyethylene glycol, succinaylated collagen, liquid collagen, and other polysaccharides or biocompatible polymers or combinations thereof. In other embodiments, the biocompatible fluid or gel. includes salts, alcohols, polyols, amino acids, sugars, proteins, polysaccharides, chondroitin sulfate, dermatan sulfate, heparin sulfate, biglycan, syndecan, keratocan, decorin, aggrecan, and combinations thereof.

Figure 2A:
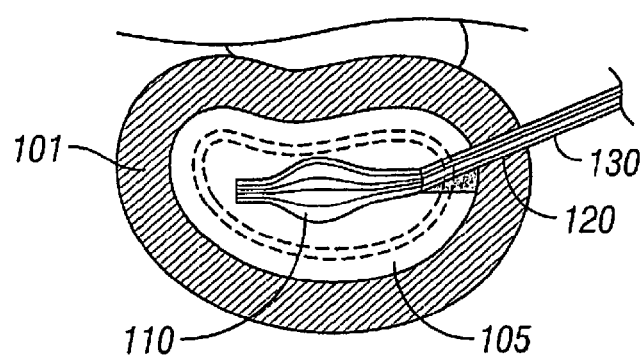
FIG. 2a illustrates a non-limiting, exemplary blown up view of the insertion of a deflated single- or multi-lumen balloon 110 into the nucleus pulposus cavity 105 using a catheter or endoscope 130, which is inserted through an injury or tear in the annulus fibrosus 120.
Figure 2B:
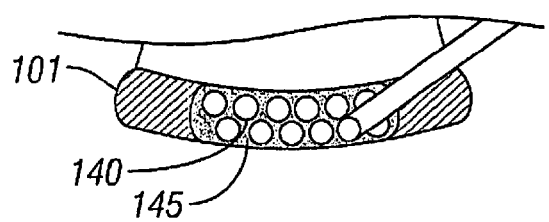
FIG. 2b illustrates the inflating of the balloon using mechanical or hydraulic means with load bearing microbeads 140 suspended in biocompatible fluid or gel.
Figure 2C:
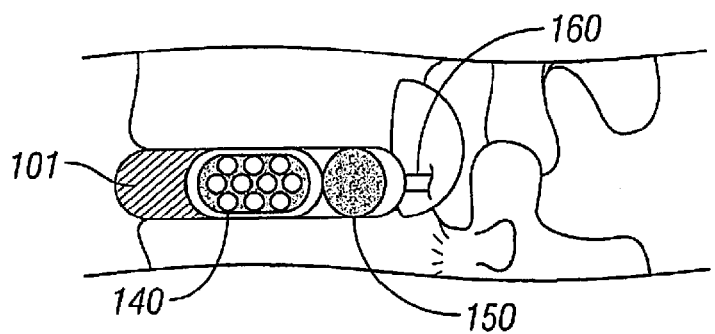
FIG. 2c illustrates the plugging of the annular injury 160 and removal of the catheter or endoscope.

FIG. 2a illustrates a non-limiting, exemplary blown up view of the insertion of a deflated single- or multi-lumen balloon 110 into the nucleus pulposus cavity 105 using a catheter or endoscope 130, which is inserted through an injury or tear in the annulus fibrosus 120. FIG. 2b illustrates the inflating of the balloon using mechanical or hydraulic means with load bearing microbeads 140 suspended in biocompatible fluid or gel 145. FIG. 2c illustrates the plugging of the annular injury 160 and removal of the catheter or endoscope.

The invention also encompasses repairing an annular tear using, for example, a resilient plug. Various materials can be utilized for this purpose, including various polymers or elastomers.

Additionally, bioactive agents can be combined with the nucleus compositions or annular material. "Bioactive agents," as used herein, include, but are not limited to, chemotactic agents; therapeutic agents (e.g., antibiotics, steroidal and non-steroidal analgesics and anti-inflammatories (including certain amino acids such as glycine), anti-rejection agents such as immunosuppressants and anti-cancer drugs); various proteins (e.g., short term peptides, bone morphogenic proteins, collagen, hyaluronic acid, glycoproteins, and lipoprotein); cell attachment mediators; biologically active ligands; integrin binding sequence; ligands; various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin derived growth factor (e.g., IGF-I, IGF-II) and transforming growth factors (e.g., TGF-β I-II) parathyroid hormone, parathyroid hormone related peptide, bone morphogenic proteins (e.g., BMP-2, BMP-4; BMP-6; BMP-7; BMP-12; BMP-13; BMP-14), sonic hedgehog, growth differentiation factors (e.g., GDF5, GDF6, GDF8), recombinant human growth factors (e.g., MP52, and MP-52 variant rhGDF-5), cartilage-derived morphogenic proteins (CDMP-1; CDMP-2, CDMP-3)); small molecules that affect the upregulation of specific growth factors; tenascin-C; hyaluronic acid; chondroitin sulfate; fibronectin; decorin; thromboelastin; thrombin-derived peptides; heparin-binding domains; heparin; heparan sulfate; DNA fragments and DNA plasmids; and combinations thereof. Suitable effectors likewise include the agonists and antagonists of the agents described above. The growth factor can also include combinations of the growth factors described above. In addition, the growth factor can be autologous growth factor that is supplied by platelets in the blood. In this case, the growth factor from platelets will be an undefined cocktail of various growth factors. If other such substances have therapeutic value in the orthopedic field, it is anticipated that at least some of these substances will have use in the present invention, and such substances should be included in the meaning of "bioactive agent" and "bioactive agents" unless expressly limited otherwise. Illustrative examples of preferred bioactive agents include culture media, bone morphogenic proteins, growth factors, growth differentiation factors, recombinant human growth factors, cartilage-derived morphogenic proteins, hydrogels, polymers, antibiotics, anti-inflammatory medications, immunosuppressive mediations, autologous, allogenic or xenologous cells such as stem cells, chondrocytes, fibroblast and proteins such as collagen and hyaluronic acid. Bioactive agents can be synthetic (e.g., bioactive glass), autologus, allogenic, xenogenic or recombinant.

In another embodiment, the invention encompasses a nucleus pulposus implant that can replace a herniated or degenerated nucleus disc. In certain embodiments, the herniated or degenerated nucleus disc is in the early stages of degenerative disc disease. In certain embodiments, the annulus fibrosus is kept intact and can maintain normal functionality.

In various embodiments, the nucleus pulposus implant is composed of a polymeric or elastomeric material that has the mechanical properties that mimic the nucleus pulposus of a healthy subject including, but not limited to, one or more biocompatible polymers of elastomers including thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain embodiments, the nucleus pulposus implant is composed of a polymeric or elastomeric material that is compressible and flexible to allow insertion and implantation endoscopically without causing the implant to substantially lose shape or form.

In other embodiments, the nucleus pulposus implant is composed of a polymeric or elastomeric material that is porous and accordingly bioactive agents as defined herein can be loaded into the implant, for example, to promote growth or to alleviate pain associated with degeneration.

In one embodiment, the nucleus implant composition comprises a single biocompatible polymeric or elastomeric material in the form of a plurality of concentric coils, wherein the outermost perimeter conforms to an inner wall of an annulus fibrosus.

Figure 3A:
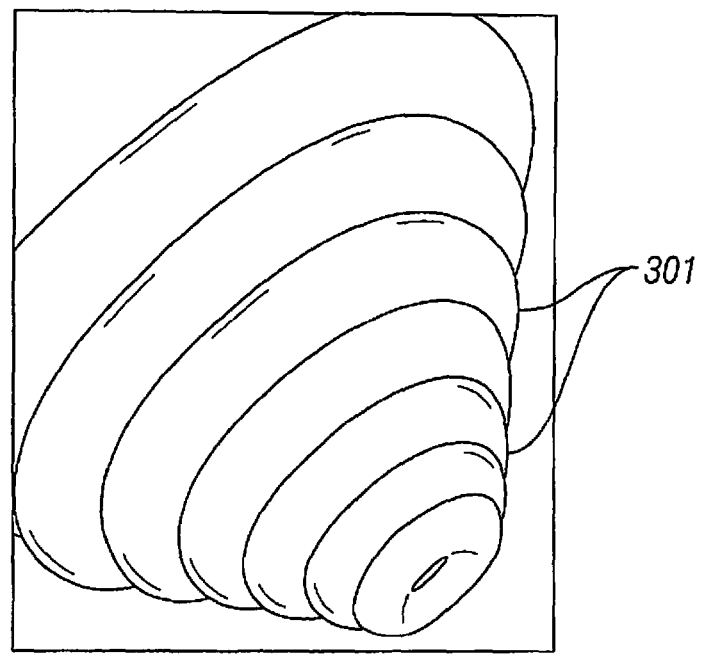
FIG. 3a illustrates a non-limiting, exemplary spring nucleus replacement comprised of one or more biocompatible polymeric or elastomeric materials in the form of a plurality of concentric coils 301 that are conically shaped. A top view in FIG. 3b illustrates a non-limiting, exemplary embodiment, wherein the concentric circles that are compressed leaving no space or very little space between the coils.
Figure 3B:
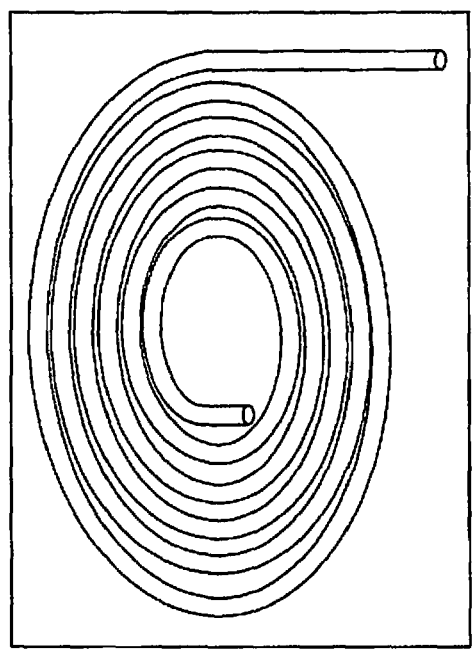

FIG. 3 illustrates a non-limiting, nucleus implant composition comprises a single biocompatible polymeric or elastomeric material in the form of a plurality of concentric coils, for example, in the shape of a spring (e.g., spring nucleus replacement composition). A top view in FIG. 3b looks like concentric circles when it is compressed leaving no space or in certain embodiments small amounts of space between the coils of the spring.

In certain embodiments, the spring nucleus replacement composition has the ability to spiral up or spiral down. In various embodiments, the spring nucleus replacement composition has the same height as the intended disc height to be restored. One skilled in the art will also consider the cross section of the spring nucleus replacement composition since contact surface area help with load/force distribution in the spine.

In certain embodiments, the outermost perimeter (i.e., the lateral sides, top and bottom surfaces) of the spring nucleus replacement composition can be rounded so that the spring nucleus replacement composition can fit firmly to the annulus fibrosus and vertebral endplate. In an illustrative embodiment, a cross section for the spring nucleus replacement composition includes a rounded rectangular figure with rounded ends as illustrated in FIG. 3b. Preferably, the outer diameter of the coil should be in contact with the annulus fibrosus.

In other illustrative embodiments, to achieve a desired disc height the more than one spring nucleus replacement composition can be inserted into the nucleus, for example, in layers.

In another embodiment, the nucleus implant composition comprises a single biocompatible polymeric or elastomeric material in the form of a pre-shaped balloon, wherein the biocompatible elastomeric or polymeric solid, deformable, and load-bearing material comprises a center cavity and one or more envelope cavities surrounding the center cavity.

In certain embodiments, the center cavity and one or more envelope cavities surrounding the center cavity can be independently filled with a plurality of elastomeric beads and/or a biocompatible fluid or gel.

In various embodiments, the nucleus implant is composed of a polymeric or elastomeric material that has the mechanical properties that mimic the nucleus pulposus of a healthy subject including, but not limited to, one or more biocompatible polymers of elastomers including thermoplastic polyurethane elastomer, poly siloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the plurality of elastomeric beads or balls include any material that is safe for in vivo use including, but not limited to, silicone, urethane, silicone-urethane copolymer, polycarbonate-urethane copolymer, polyethylene terephthalate, or combinations thereof.

In other illustrative embodiments, the biocompatible fluid or gel include any material that is safe for in vivo use including, but not limited to, saline, beta-glucan, hyaluronic acid and derivatives thereof, polyvinyl pyrrolidone or a hydrogel derivative thereof, dextrans or a hydrogel derivative thereof, glycerol, polyethylene glycol, succinaylated collagen, liquid collagen, and other polysaccharides or biocompatible polymers or combinations thereof. In other embodiments, the biocompatible fluid or gel. includes salts, alcohols, polyols, amino acids, sugars, proteins, polysaccharides, chondroitin sulfate, dermatan sulfate, heparin sulfate, biglycan, syndecan, keratocan, decorin, aggrecan, and combinations thereof.

Figure 4A:
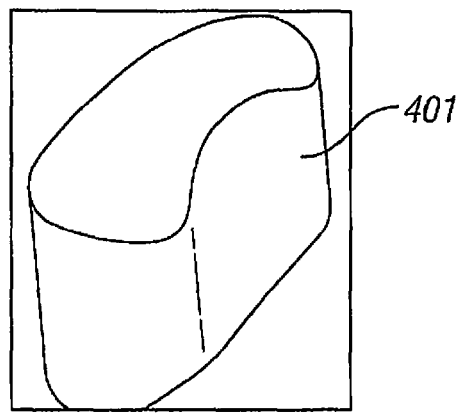
FIG. 4a illustrates a non-limiting, exemplary pre-shaped balloon nucleus replacement composition 401 that can be created to conform to the intervertebral disc levels (e.g., L1-S1). In certain illustrative embodiments, the shape and height can be cut by a surgeon to conform the intervertebral disc height. In certain non-limiting, exemplary embodiments.
Figure 4B:
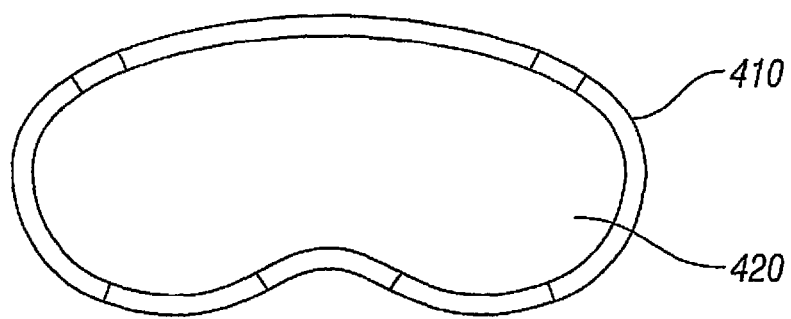
FIG. 4b illustrates a single envelope system, which allows filling the envelope cavity space 410, the center cavity 420, or both of them.

FIG. 4a illustrates a non-limiting, exemplary pre-shaped balloon nucleus replacement that can be created to conform to the intervertebral disc levels (e.g., L1-S1). In certain non-limiting, exemplary embodiments, FIG. 4b illustrates a multiple envelope system that allows filling the envelope cavity space, the center cavity or both of them. In certain embodiments, the biocompatible materials that can be used to fill the center or the envelope cavity include beads or saline.

Another embodiment encompasses a nucleus replacement composition comprised of one or more biocompatible elastomeric or polymeric materials in the shape of a plurality of string-like implants. In various embodiments, the nucleus implant is composed of a polymeric or elastomeric material that has the mechanical properties that mimic the nucleus pulposus of a healthy subject including, but not limited to, one or more biocompatible polymers of elastomers including thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

Figure 5A:
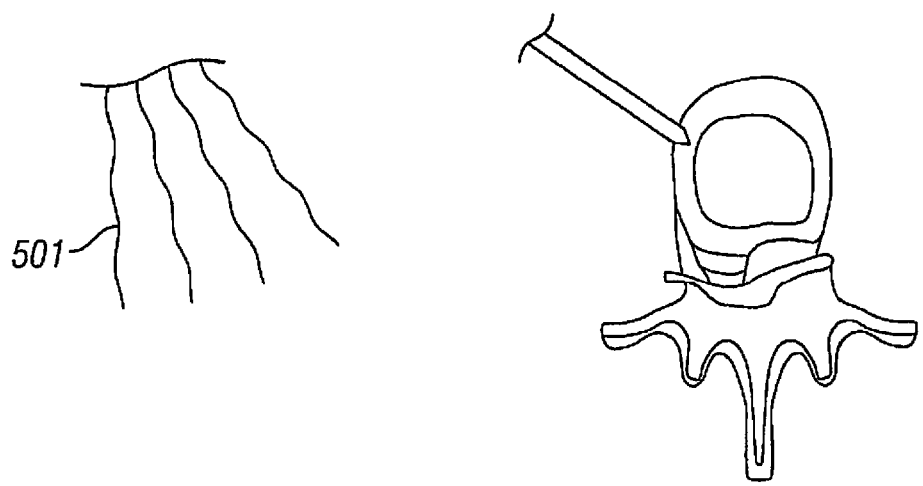
FIG. 5a illustrates a non-limiting, exemplary thin string nucleus implant composition 501. The thin string can be implanted through a tear or fissure in the annulus fibrosus and in illustrative embodiments the string is larger than the tear or fissures to prevent leakage.
Figure 5B:
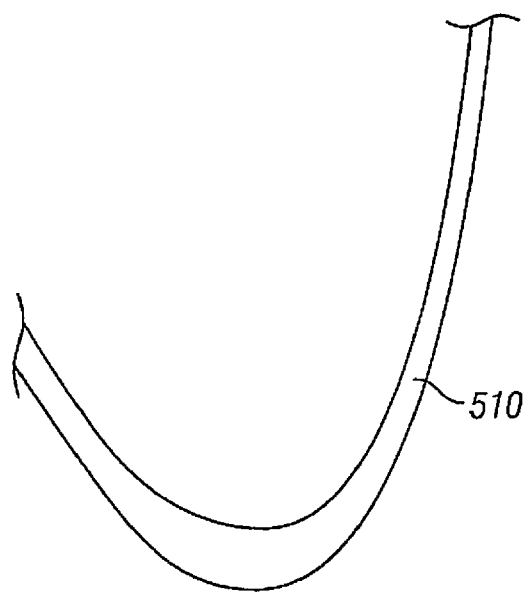
FIG. 5b illustrates a blown up view of a thin string 510.

FIG. 5a illustrates a non-limiting, exemplary thin string nucleus implant design. The thin string can be implanted through a tear in the annulus fibrosus and in illustrative embodiments the string is larger than the tear or fissures to prevent leakage. FIG. 5b illustrates a blown up view of a thin string.

In certain embodiments, the implant will include a plurality of thin strings. In certain embodiments, the diameter of the strings is larger than the fissures/tears and annulotomy in the annulus so that upon entry in the IVD to fill the nucleus so it does not exit or effuse. The string can be comprised of tiny microbeads made into a string form or a cylindrical string form.

In an illustrative embodiment, the method of insertion of the implant it through a cannula. The string will then be injected into the nucleus cavity and then the string expands out into the nucleus cavity. In certain embodiments, this eliminates the need for annular repair.

In another embodiment, the invention encompasses a nucleus pulposus containment shell comprising a containment jacket including a nucleus pulposus filler material that provides minimally invasive surgical port delivery, includes a containment jacket of known geometry and mechanical properties, filler material that maintains known pressure and prevents future expulsion, and includes anchorage to the vertebral endplates.

One illustrative embodiment encompasses a nucleus pulposus containment shell comprising:
  a. an outer shell comprised of a biocompatible material;
  b. an inner surface capable of being filled with a load bearing polymeric or elastomeric material,
  c. a unidirectional valve for filling the inner surface; and
  d. a sealing crimp to prevent leakage of the load bearing polymeric or elastomeric material filling the inner surface.
wherein the outer shell has an cylindrical-like shape, wherein a top surface and/or a bottom surface are textured to provide anchorage with vertebral endplates.

Another illustrative embodiment encompasses a nucleus pulposus containment shell comprising:
  a. an outer shell comprised of a biocompatible material;
  b. an inner surface capable of being filled with a load bearing polymeric or elastomeric material,
  c. a unidirectional valve for filling the inner surface; and
  d. a sealing crimp to prevent leakage of the load bearing polymeric or elastomeric material filling the inner surface.
wherein the outer shell has an tubular ring-like shape, wherein a top surface and/or a bottom surface are textured to provide anchorage with vertebral endplates.

In certain illustrative embodiments, the containment shell is comprised of (1) metals (e.g., titanium or titanium alloys, alloys with cobalt and chromium, cobalt-chrome, stainless steel); (2) plastics (e.g., ultra-high molecular weight polyethylene (UHMWPE), polymethylmethacrylate (PMMA), polytetrafluoroethylene (PTFE), polyetheretherketone (PEEK), nylon, polypropylene, and/or PMMA/polyhydroxy-ethylmethacrylate (PHEMA)); (3) ceramics (e.g., alumina, beryllia, calcium phosphate, and/or zirconia, among others); (4) composites; and/or the like. In some embodiments, the containment shell is a metal foil shell. In certain embodiments, the materials may be partially or completely bio-resorbable as desired or appropriate.

In other illustrative embodiments, the containment shell can include a partially or totally textured surface to allow anchorage with the vertebral endplates. As used herein, textured, refers to any grooved or rough texture (e.g., a Velcro®-like texture) or porous features that increases the friction and anchorage with the vertebral endplates.

Figure 6A:
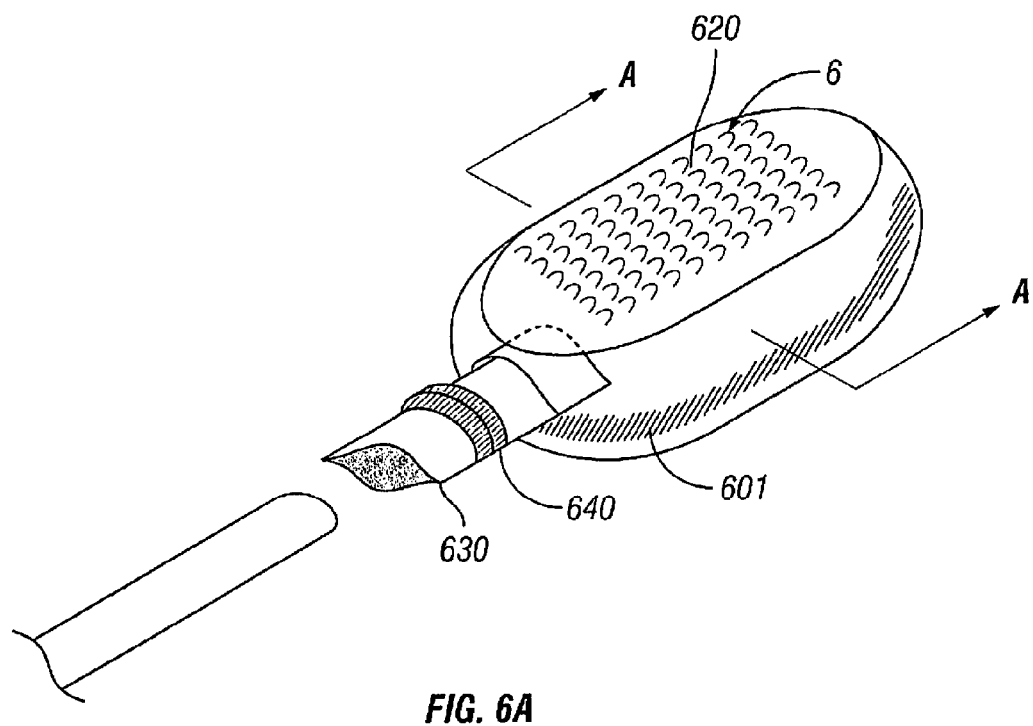
FIGS. 6a and 6b illustrate a non-limiting, exemplary nucleus pulposus containment shell including an outer shell having a cylindrical or ellipsoid-like shape (i.e., having a curved diameter 601 and flattened top and/or bottom surface 610). In certain embodiments, the nucleus pulposus containment shell includes a textured top and/or bottom surface 620 to provide anchorage with vertebral endplates and an optionally textured surface along the curved perimeter. The implant can be filled with a load bearing polymeric or elastomeric material filling to allow the implant to conform to the shape of the annulus fibrosus 6b. In an illustrative, non-limiting embodiment, the implant is comprised of a metal foil shell or polymer shell (e.g., urethanes, silicones), or a combination thereof, a unidirectional valve 630 for filling the inner surface; and a sealing crimp 640 to prevent leakage of the load bearing polymeric or elastomeric material filling the inner surface.
Figure 6B:
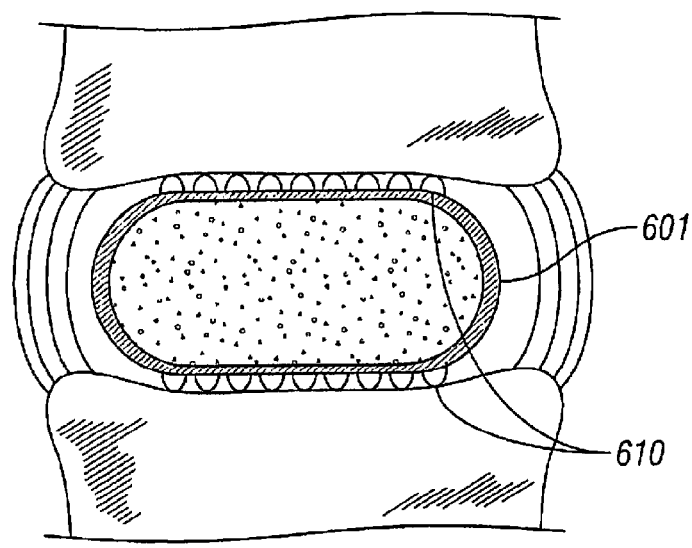

FIGS. 6a and 6b illustrate a non-limiting, exemplary nucleus pulposus containment shell including an outer shell having a cylindrical shape and a textured top and bottom surface to provide anchorage with vertebral endplates. The implant can be filled with a load bearing polymeric or elastomeric material filling to allow the implant to conform to the shape of the annulus fibrosus. The illustrative, non-limiting implant includes a metal foil shell or polymer shell (e.g., urethanes, silicones), or a combination thereof, a unidirectional valve for filling the inner surface; and a sealing crimp to prevent leakage of the load bearing polymeric or elastomeric material filling the inner surface.

Figure 7A:
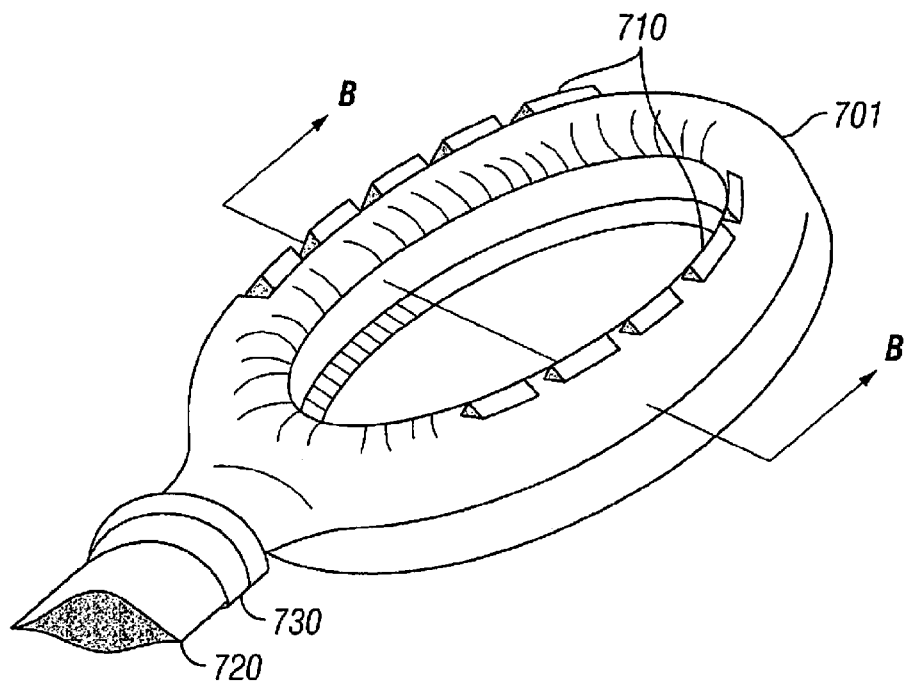
FIGS. 7*a*-7*c* illustrate a non-limiting, exemplary nucleus pulposus containment shell including an outer shell having a tubular ring-like shape and a textured top and bottom surface to provide anchorage with vertebral endplates and an optionally textured surface along the curved perimeter. The implant can be filled with a load bearing polymeric or elastomeric material filling to allow the implant to conform to the shape of the annulus fibrosus. In an illustrative, non-limiting embodiment, the implant includes a metal foil shell or polymer shell (e.g., urethanes, silicones), or a combination thereof, a unidirectional valve for filling the inner surface; a unidirectional valve 720 for filling the inner surface; and a sealing crimp 730 to prevent leakage of the load bearing polymeric or elastomeric material filling the inner surface.
Figure 7B:
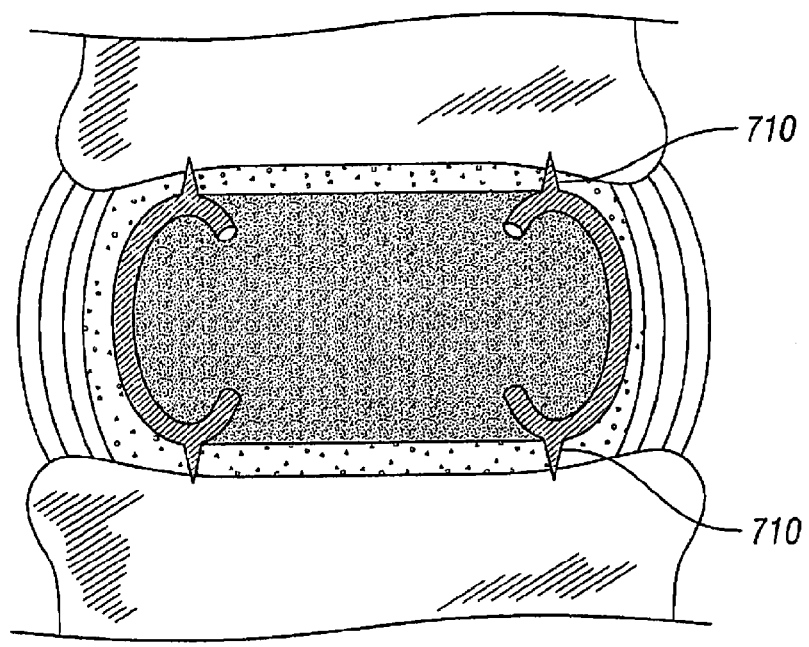
Figure 7C:
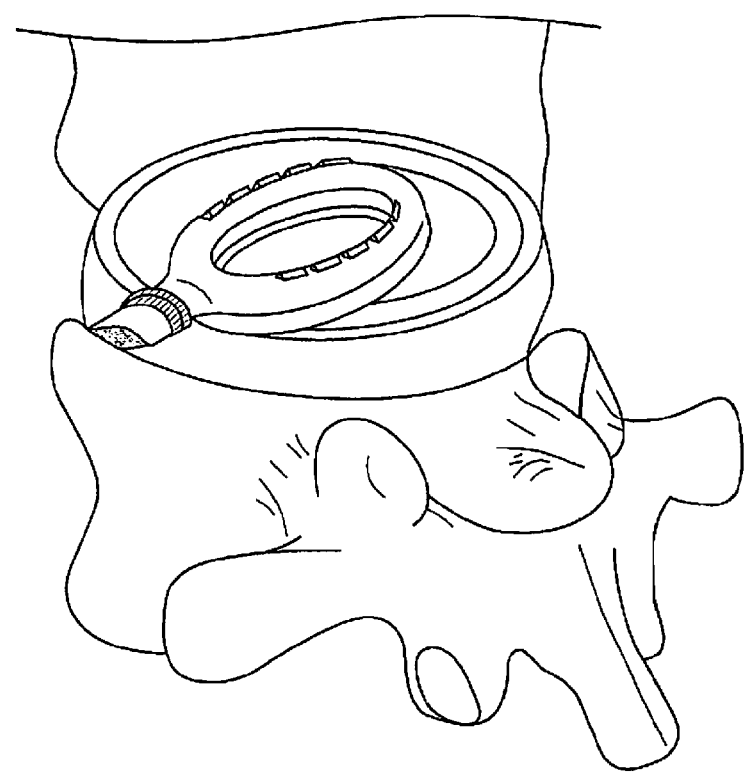
Figure 8:
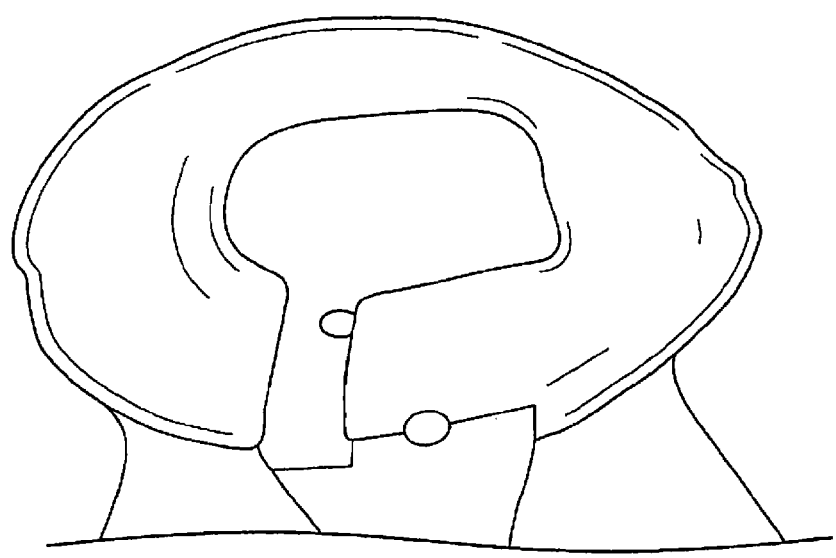
FIG. 8 illustrates a non-limiting, exemplary annulus fibrosus including an opening wherein the nucleus pulposus has been removed to create a cavity in the annulus fibrosus. Through the opening a nucleus pulposus replacement composition of the invention can be inserted into the annulus fibrosus.
Figure 9A:
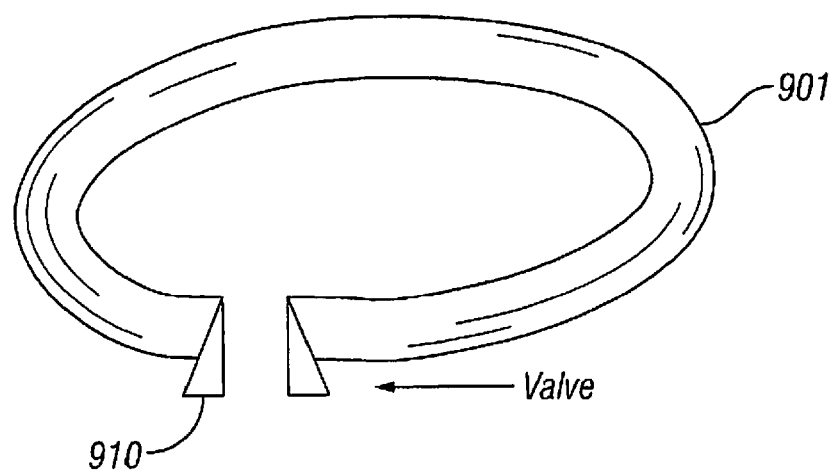
FIG. 9*a* illustrates a non-limiting, exemplary nucleus pulposus implant 901 comprised of a biocompatible polymeric or elastomeric material and including a valve that allows the implant to be filled, for example, with a load bearing polymeric or elastomeric material after insertion into the annulus fibrosus cavity. The valve can include a rigid socket geometry 910 for connecting with an annulus fibrosus plug that includes a ball fitting that connects with the valve of the nucleus implant.
Figure 9B:
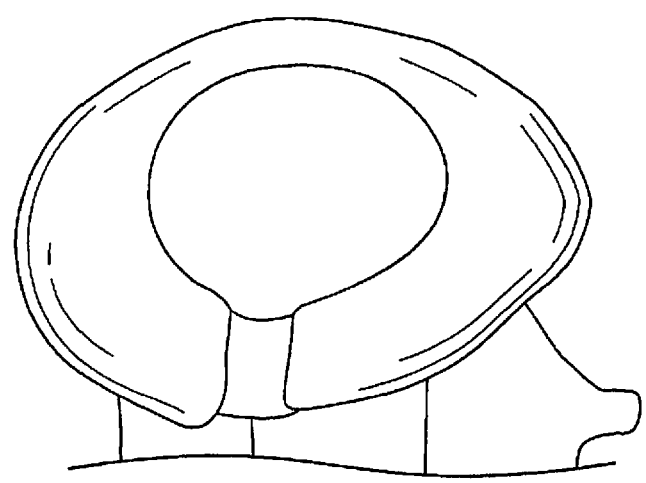
FIG. 9*b* illustrates a non-limiting, exemplary example of the nucleus pulposus implant inserted into the cavity of the annulus fibrosus.

FIGS. 7a-7c illustrates a second non-limiting, exemplary nucleus pulposus containment shell including an outer shell having a tubular ring-like shape and a textured top and bottom surface to provide anchorage with vertebral endplates. The implant can be filled with a load bearing polymeric or elastomeric material filling to allow the implant to conform to the shape of the annulus fibrosus. The illustrative, non-limiting implant includes a metal foil shell, a unidirectional valve for filling the inner surface; and a sealing crimp to prevent leakage of the load bearing polymeric or elastomeric material filling the inner surface.

In certain embodiments, the load bearing polymeric or elastomeric material is a thermoplastic polyurethane elastomer, poly siloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, silicone, urethane, silicone-urethane copolymer, polycarbonate-urethane copolymer, polyethylene terephthalate, saline, beta-glucan, hyaluronic acid and derivatives thereof, polyvinyl pyrrolidone or a hydrogel derivative thereof, dextrans or a hydrogel derivative thereof, glycerol, polyethylene glycol, succinaylated collagen, liquid collagen, and other polysaccharides or biocompatible polymers or combinations thereof.

Generally, the nucleus containment shell includes a unidirectional valve to allow filling of the containment shell with the load bearing polymeric or elastomeric material. In addition, the nucleus containment shell includes a sealing crimp to prevent leakage of the load bearing polymeric or elastomeric material.

In another embodiment, the invention encompasses a combination nucleus pulposus replacement and annulus fibrosus repair system comprising:
  a. nucleus replacement composition comprising:
   i. an outer surface comprised of a biocompatible material and adapted to conform to an inner wall of an annulus fibrosus and comprising a valve attached to the outer surface comprising a rigid socket geometry; and
   ii. an inner surface having a central recess capable of receiving a load bearing polymeric or elastomeric material,
  wherein the outer and inner surfaces define a solid, deformable thickness therebetween; and
  b. an annulus fibrosus plug comprising a ball fitting (or other shaped fitting) that connects with the valve of the nucleus replacement composition, wherein the ball fitting (or other shaped fitting) comprises a plug of a natural or synthetic material that promotes cell in-growth (e.g., a fibrous or woven structure that includes a cell growth media) with the surrounding annulus fibrosus.

In certain embodiments, the repair system includes a guide for inserting and/or connecting the annulus fibrosus plug with the nucleus replacement composition. In certain embodiments, the rigid socket geometry is comprised of a metal, a plastic (e.g., polyether ether ketone) or a combination thereof.

In certain embodiments, the valve attached to the outer surface comprises a rigid socket geometry (i.e., a female part) that can mate with a rigid ball (or other shape, for example, elliptical) geometry of the annulus plug (i.e., a male part).

The nucleus pulposus replacement composition can be comprised of any durable material that is safe for in vivo transplantation including, but not limited to, one or more biocompatible polymers of elastomers including thermoplastic polyurethane elastomer, polysiloxane modified styrene-ethylene/butylene block copolymer, polycarbonate-urethane, polycarbonate-urethane cross-linked by a polyol, silicone rubber, silicone elastomer, polyether urethane, polyester urethane, a polyether polyester copolymer, polypropylene oxide, and combinations thereof.

In certain illustrative embodiments, the load bearing polymeric or elastomeric material includes a plurality of elastomeric beads or balls suspended in a biocompatible fluid or gel.

In certain illustrative embodiments, the plurality of elastomeric beads or balls include any material that is safe for in vivo use including, but not limited to, silicone, urethane, silicone-urethane copolymer, polycarbonate-urethane copolymer, polyethylene terephthalate, or combinations thereof.

In other illustrative embodiments, the biocompatible fluid or gel include any material that is safe for in vivo use including, but not limited to, saline, beta-glucan, hyaluronic acid and derivatives thereof, polyvinyl pyrrolidone or a hydrogel derivative thereof, dextrans or a hydrogel derivative thereof, glycerol, polyethylene glycol, Pluronic® type block copolymers (i.e., based on ethylene oxide and propylene oxide), succinaylated collagen, liquid collagen, and other polysaccharides or biocompatible polymers or combinations thereof. In other embodiments, the biocompatible fluid or gel. includes salts, alcohols, polyols, amino acids, sugars, proteins, polysaccharides, chondroitin sulfate, dermatan sulfate, heparin sulfate, biglycan, syndecan, keratocan, decorin, aggrecan, and combinations thereof. In other embodiments, the fluid or gel includes in situ curable materials, for example, polyurethanes and silicones) that will form a solid in situ.

Figure 10A:
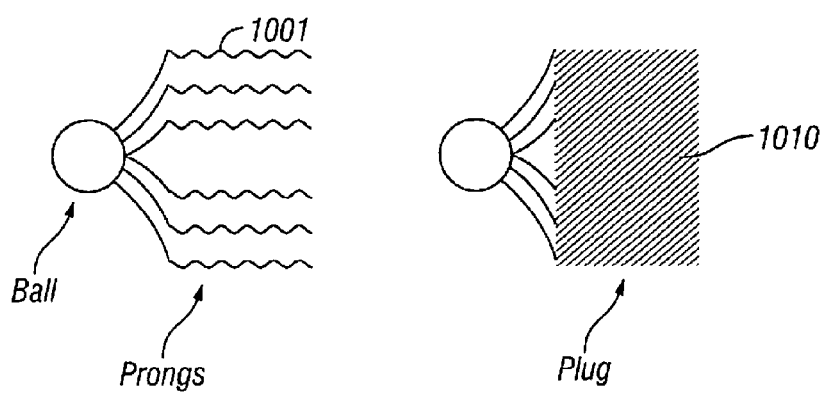
FIG. 10*a* illustrates a non-limiting, exemplary annulus fibrosus plug including a weave of fibers 1001 or a sponge 1010 (i.e., a natural or synthetic material) to make a porous plug that is permanently attached to the prongs on the plug. The porous plug promotes in vivo cell in-growth from the surrounding annulus.
Figure 11:
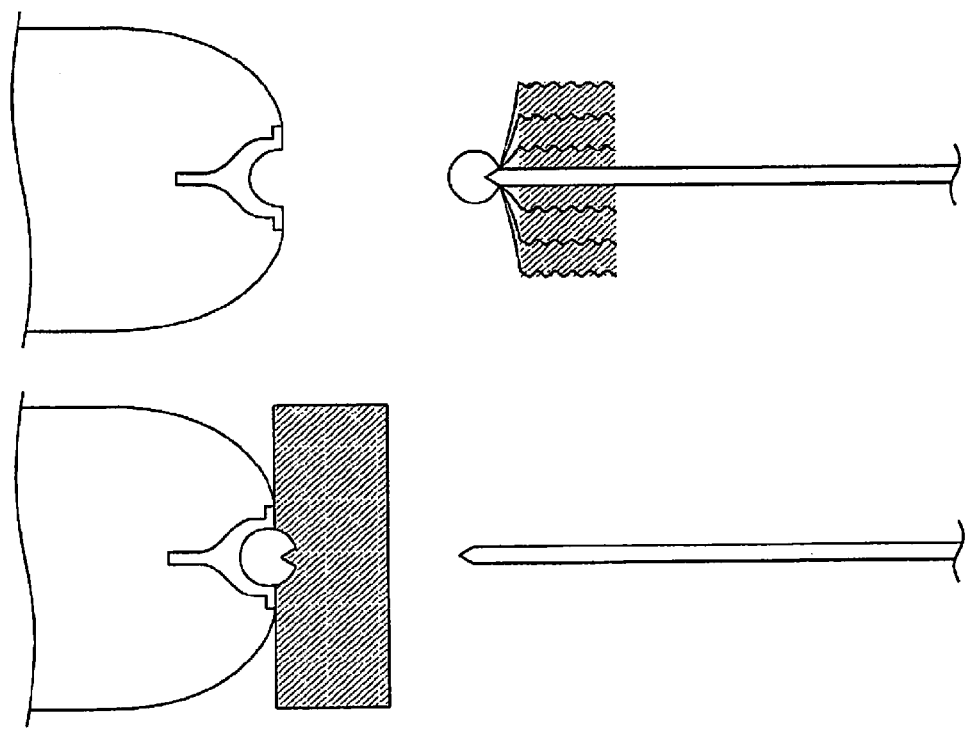
FIG. 11 illustrates a non-limiting, exemplary schematic of a nucleus pulposus implant including a check valve that can be attached an annulus fibrosus plug. The annulus fibrosus plug is connected to the nucleus pulposus valve using a guide that is connected to the annulus fibrosus plug. After attaching the annulus fibrosus plug to the nucleus pulposus implant the guide can be removed by mechanical (e.g., by unscrewing) or hydraulic means.

In certain illustrative embodiments, the annulus fibrosus plug is attached to a ball fitting (or other shaped fitting) that allows connection with the nucleus replacement composition. FIG. 11 illustrates a schematic of insertion of the annulus plug into the nucleus replacement composition using a removable guide. In certain embodiments, the annulus plug material can be comprised of a weave of fibers or a sponge (i.e., a natural or synthetic material) as illustrated in FIG. 10a to make a porous plug that permits or promotes in vivo cell in-growth from the surrounding annulus and accordingly can include a bioactive agent.

Figure 12A:
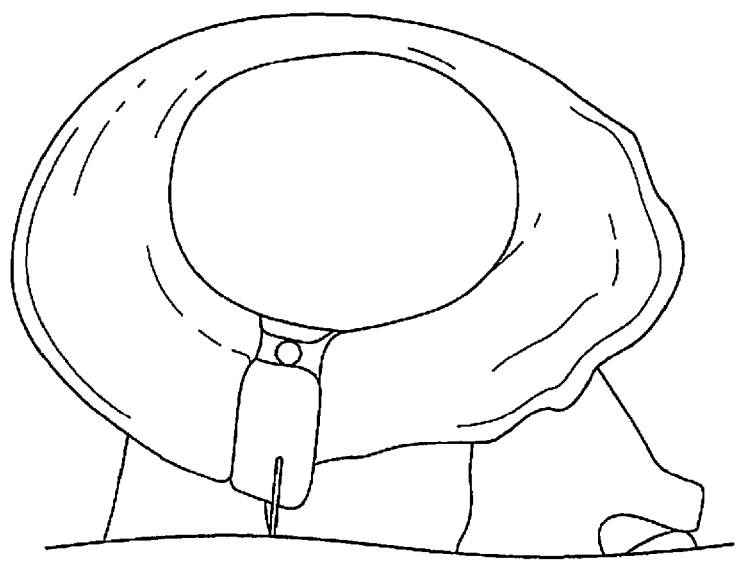
FIG. 12*a* illustrates a non-limiting, exemplary embodiment of a nucleus pulposus implant including a check valve just prior to attachment of annulus fibrosus plug. The annulus fibrosus plug is attached to a guide and is inserted into the annulus fibrosus tear or fissure.
Figure 12B:
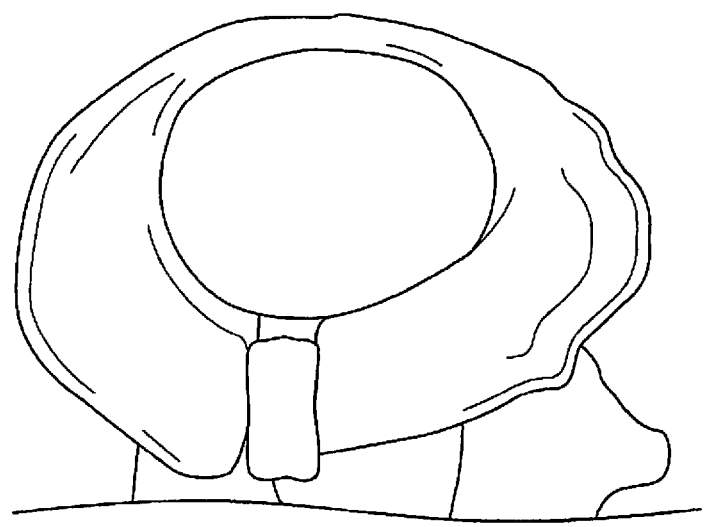
FIG. 12*b* illustrates a non-limiting, exemplary embodiment of a nucleus pulposus implant including a check valve and the attachment of annulus fibrosus plug. The annulus fibrosus plug is attached to a guide and being inserted into the annulus fibrosus tear, to engage with the socket of the check valve.

FIGS. 12a and 12b illustrate a non-limiting, exemplary embodiment of a nucleus pulposus implant including a check valve just prior to attachment of annulus fibrosus plug. The annulus fibrosus plug is attached to a guide and being inserted into the annulus fibrosus tear.

Kits

Figure 10B:
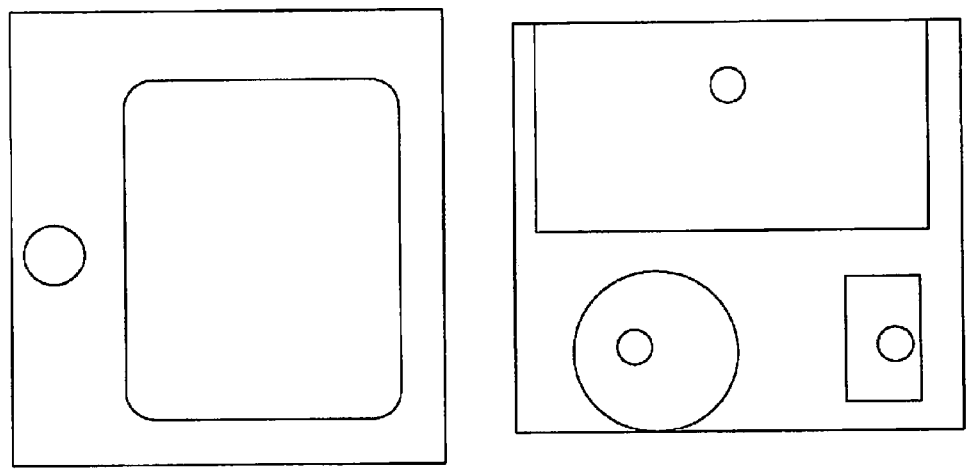
FIG. 10*b* illustrates a non-limiting, exemplary annulus fibrosus plug that is preformed with different plug geometries that allow a surgeon to cut the plug from stock size plugs to suit a particular annulus fibrosus defect size.

The invention also contemplates kits including a nucleus replacement composition and an annulus fibrosus plug and the equipment and materials required to insert the composition into the intervertebral cavity. FIG. 10b illustrates annulus fibrosus plugs of varying sizes that can be cut by a surgeon to seal a tear or cut in the subject's annulus fibrosus.

Accordingly, the nucleus replacement composition and an annulus fibrosus can be manufactured in varying widths, lengths, and dimensions to accommodate the type of surgery and needs of the surgeon.

In addition, the kits can also include the load bearing polymeric or elastomeric material including a plurality of elastomeric beads or balls suspended in a biocompatible fluid or gel and the necessary cannulas to administer them.

The kits of the invention are intended to broaden a surgeon's options once in surgery to provide a patient with the most optimal nucleus replacement composition and annulus fibrosus repair technology.

EXAMPLES

Example 1

To repair a herniated disk injury, nucleus material leaking from an opening in the annulus fibrosus is removed in a surgical operation to form a nucleus cavity. This may be carried out with, for example, a forceps-like instrument with which the jelly-like nucleus material is cut off and the opening may also be enlarged and its edges smoothed. The thus removed nucleus material may be used for growing a culture of the patient's own body cells.

A nucleus pulposus replacement composition is then inserted through the opening in the annulus and into the nucleus cavity. The nucleus pulposus replacement composition includes, for example, a biocompatible solid, deformable, load-bearing material in the form of a balloon, which is deflated and incorporated into the nucleus cavity using a catheter and is selected in relation to the size of the opening such that upon introducing the nucleus pulposus replacement composition into the opening, the opening is not unnecessarily enlarged. The nucleus pulposus replacement composition may have, for example, the shape of a relatively narrow rectangular parallelepiped. The nucleus pulposus replacement composition is connectable by a rod to a handle which can be removed, for example, by unscrewing.

After insertion of the nucleus pulposus replacement composition, the composition can be filled with, for example, a plurality of elastomeric beads suspended in a biocompatible fluid or gel. The amount of beads and gel can be determined by the surgeon during surgery and depends on the patient's physiology, the location on the vertebra of the implant, and other mechanical and physical properties apparent to the surgeon.

The annulus fibrosus plug comprising a ball fitting (or other shaped fitting) is then inserted into the tear or incision in the annulus of the patient. The annulus fibrosus plug connects with a check valve of the nucleus replacement composition, wherein a ball fitting comprises a plug of a natural or synthetic material that promotes cell in-growth (e.g., a fibrous or woven structure that includes a cell growth media) with the surrounding annulus fibrosus.

The annulus fibrosus plug is pushed into the opening using a suitable insertion instrument, which releasably grips the implant. Once the annulus fibrosus plug has been pushed fully into the opening, the insertion instrument may be released and removed. As will be apparent, the annulus fibrosus plug now closes the opening in the patient's annulus and is supported at its upper face on the end plate of an upper vertebra and at its lower face on the end plate of a lower vertebra.

In various embodiments, the annulus fibrosus plug comprises of a resorbable material and is porous. The size of the pores is between about 50 μm and about 500 μm. The material of the plug-shaped implant is flexible and elastic, so that it adapts optimally to the contour of the opening and also easily follows the movements of the material of the annulus fibrosus. The nucleus pulposus replacement is less deformable or elastic in the same way as the rest of the material of the implant. This results in a rigid connection in the area in which the implant is fixed to the adjacent vertebrae. The material of the implant adapts to the movability of the material of the annulus fibrosus and reliably closes the opening.

In this way, the entire material of the plug may be flexible or elastic, but it is also possible for the material of the plug to become progressively firmer. When the opening in the annulus fibrosus has been closed in this way, cell material grown outside of the body (e.g., in a culture) can be introduced into the interior of the intervertebral disc. For example, this is carried out approximately weeks after the surgical operation described above. Alternatively, the porous annulus fibrosus can be coated with a bioactive agent that promotes cell growth or provides a therapeutic effect.

In the specification, there have been disclosed typical preferred embodiments of the invention and, although specific terms are employed, they are used in a generic and descriptive sense only and not for purposes of limitation. Obviously many modifications and variations of the invention are possible in light of the above teachings. It is therefore to be understood that the invention may be practiced otherwise than as specifically described.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited above are incorporated herein by reference to the extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A nucleus pulposus replacement device comprising:
   an outer shell comprised of a biocompatible material defining a central fillable cavity having a central cavity and one or more envelope cavities completely surrounding an outer perimeter of the central cavity;
   an inner surface capable of receiving a load bearing polymeric or elastomeric material;
   a valve to allow filling of the inner surface; and
   a sealing crimp.

2. The device of claim 1, wherein device is insertable with an endoscope.

3. The device of claim 1, wherein the outer shell is comprised of a metallic material.

4. The device of claim 3, wherein the metallic material comprises NiTi alloy, stainless steel, titanium, or combinations thereof.

5. The device of claim 1, wherein the outer shell is comprised of a polymeric material.

6. The device of claim 1, further comprising filling the inner surface with the load bearing polymeric or elastomeric material, wherein the load bearing polymeric or elastomeric material includes a plurality of elastomeric beads or balls suspended in a biocompatible fluid or gel.

7. The device of claim 6, wherein the plurality of elastomeric beads or balls comprises silicone, urethane, silicone-urethane copolymer, polycarbonate-urethane copolymer, polyethylene terephthalate, or combinations thereof.

8. The device of claim 1, wherein the valve comprises a unidirectional valve.

9. The device of claim 1, wherein the nucleus pulposus replacement device is cylindrically shaped.

10. The device of claim 1, wherein the nucleus pulposus replacement device includes a textured top surface and a textured bottom surface.

11. A method of surgery comprising:
    removing at least a portion of a nucleus pulposus through an annulus fibrosus to create a cavity;
    inserting a nucleus pulposus replacement device in the cavity, wherein the device comprises:
       an outer shell comprising a tubular ring having a top surface, a bottom surface, and lateral sides comprised of a biocompatible material;
       an inner surface capable of receiving a load bearing polymeric or elastomeric material; and
       a valve to allow filling of the inner surface;
    wherein, when inflated with the load bearing polymeric or elastomeric material, the top and bottom surfaces and lateral sides of the tubular ring are rounded so that the nucleus pulposus replacement device is configured to fit firmly to the annulus fibrosus and vertebral endplates.

12. The method of claim 11, wherein inserting the nucleus pulposus replacement device is performed using an endoscope.

13. The method of surgery of claim 11, wherein the outer shell is comprised of a metallic material.

14. The method of surgery of claim 13, wherein the metallic material comprises NiTi alloy, stainless steel, titanium, or combinations thereof.

15. The method of surgery of claim 11, wherein the outer shell is comprised of a polymeric material.

16. The method of surgery of claim 11, further comprising filling the inner surface with the load bearing polymeric or elastomeric material, wherein the load bearing polymeric or elastomeric material includes a plurality of elastomeric beads or balls suspended in a biocompatible fluid or gel.

17. The method of claim 16, wherein the plurality of elastomeric beads or balls comprises silicone, urethane, silicone-urethane copolymer, polycarbonate-urethane copolymer, polyethylene terephthalate, or combinations thereof.

18. The method of claim 11, wherein the valve comprises a unidirectional valve.

19. The method of claim 11, wherein the nucleus pulposus replacement device is cylindrically shaped.

20. The method of claim 11, wherein the nucleus pulposus replacement device includes a textured top surface and a textured bottom surface.

* * * * *